United States Patent [19]
Caillouette

[11] Patent Number: 5,782,801
[45] Date of Patent: Jul. 21, 1998

[54] CONTROLLED APPLICATION OF CONTAINED SCREENING OR TREATMENT FLUID TO TISSUE SUCH AS CERVICAL OR VAGINAL TISSUE

[76] Inventor: James C. Caillouette, 685 Oak Knoll Circle, Pasadena, Calif. 91106

[21] Appl. No.: 789,835

[22] Filed: Jan. 31, 1997

[51] Int. Cl.⁶ .................................................. A61M 31/00
[52] U.S. Cl. ................................ 604/55; 604/54; 604/3; 604/271
[58] Field of Search ........................... 604/55, 54, 1, 604/2, 3, 290, 271

[56] References Cited

U.S. PATENT DOCUMENTS

| | | |
|---|---|---|
| 2,664,879 | 1/1954 | Hardy . |
| 2,945,491 | 7/1960 | Gibbs . |
| 3,037,496 | 6/1962 | Melges . |
| 3,117,569 | 1/1964 | Wegner . |
| 3,319,621 | 5/1967 | Schwerin . |
| 3,507,269 | 4/1970 | Berry . |
| 3,509,872 | 5/1970 | Truhan . |
| 3,614,245 | 10/1971 | Schwartzmon ............... 604/3 |
| 4,820,259 | 4/1989 | Stevens . |
| 4,862,899 | 9/1989 | Bucaro . |
| 5,063,930 | 11/1991 | Nucci . |
| 5,147,288 | 9/1992 | Schiavo . |

Primary Examiner—Michael Buiz
Assistant Examiner—N. Kent Gring
Attorney, Agent, or Firm—William W. Haefliger

[57] ABSTRACT

In the method of applying screening or treatment fluid to the cervix, vagina, or other genital tissues, the steps include providing an elongated assembly including an elongated carrier and a flexible outer container supported on the carrier; providing a fluid applicator at one end of the assembly to communicate with the interior of the outer container; providing a frangible inner container protectively located within the outer container, and providing screening or treatment fluid within the inner container, exerting pressure on the outer container sufficient to rupture the inner container, thereby releasing the screening or treatment fluid into the interior of the outer container, enabling fluid migration to the applicator, and manipulating said assembly to cause the applicator to apply screening or treatment fluid to the cervix, vagina, or other genital tissues.

18 Claims, 3 Drawing Sheets

CONTROLLED APPLICATION OF CONTAINED SCREENING OR TREATMENT FLUID TO TISSUE SUCH AS CERVICAL OR VAGINAL TISSUE

BACKGROUND OF THE INVENTION

This invention relates generally to screening or treatment of body parts, and more particularly to method and apparatus for easily and quickly applying treatment fluid to tissue such as that of the cervix, vagina, or vulva as well as other body parts which may normally be concealed.

There is need for simple, easily used apparatus for reliably and quickly applying screening or treatment fluid or liquid to body parts, for example the cervix. Such fluid may be test fluid for use in cancer detection. There is also need for simple, effective methods to locally apply such fluids. Prior apparatus and techniques were cumbersome, and lacked the unusual advantages disclosed herein. Fluids used may degrade quickly after being exposed to air.

SUMMARY OF THE INVENTION

It is a major object of the invention to provide improvements in method and apparatus meeting the above needs. Basically, the method of the invention includes the following steps:

a) providing an elongated assembly including an elongated carrier and a flexible outer container supported on the carrier, b) providing a fluid applicator at one end of the assembly to communicate with the interior of the outer container, c) providing a frangible inner container protectively located within the outer container, and providing screening or treatment fluid within the inner container, d) exerting pressure on the outer container sufficient to rupture the inner container, thereby releasing contained fluid into the interior of the outer container, enabling fluid migration to the applicator, e) and manipulating the assembly when inserted into the vaginal cavity to cause the applicator to apply the screening or treatment fluid to tissue surfaces such as those of the cervix and/or vagina.

As will be seen, the screening or treatment fluid stored within the inner container may advantageously consist essentially of iodine, used in cervical screening for cancer or pre-cancer detection.

Another object comprises providing the outer container in close association with the applicator such as a swab, the outer container for example located between the end of a carrier stick and the applicator itself, whereby the contained fluid when released into the outer container interior is directly accessible to the applicator to be locally applied to the tissue, as by manipulation of the carrier stick. Alternatively, the outer container may be provided on the carrier stick at a location relatively remote from the applicator or swab. In that event, a duct may be provided to be associated with the carrier to convey fluid from the container interior to the applicator. Controllable manual pressure on the outer compressible container, after breakage of the inner glass or rigid container, controls flow of the fluid to the applicator or swab.

Yet another object is to employ manual pressure exertion on the outer container to flex its wall or walls for pressurizing the inner container to fracture its wall. The outer container may consist of leak proof plastic, and the inner container of thin walled glass, i.e. it is frangible.

Yet another step is to manipulate the assembly to cause the outer container to exert endwise and sidewise force on the applicator to cause the applicator to apply test fluid to local surface area of the cervix.

An additional object is to observe the tissue color change indicating cancer or pre-cancer cells' presence.

In this regard, normal cervical or vaginal mucous membrane contains glycogen, whereas abnormal such membrane or tissue, (for example pre-cancerous tissue) does not contain glycogen. Iodine application causes the normal tissue to become dark mahogany in color, whereas abnormal tissue remains pink. If weak acetic acid is used (about 5% solution) instead of the iodine solution, it causes abnormal tissue to take on a whitish appearance, whereas normal tissue does not take on that coloration.

These and other objects and advantages of the invention, as well as the details of an illustrative embodiment, will be more fully understood from the following specification and drawings, in which:

DRAWING DESCRIPTION

DETAILED DESCRIPTION

Figure 1:
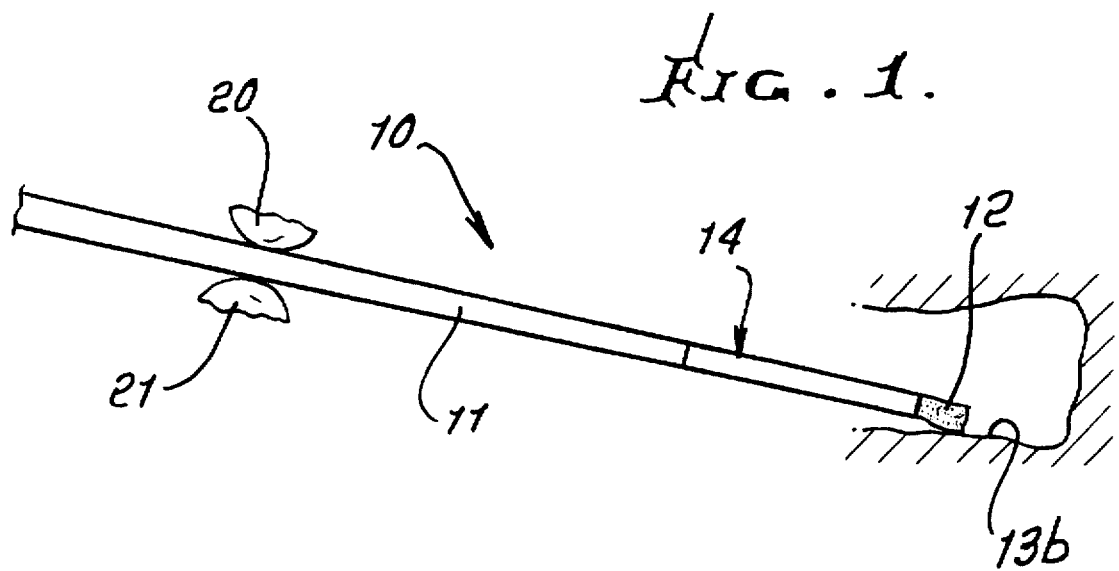
FIG. 1 is a view showing use of an elongated assembly incorporating the invention.

In FIG. 1 an elongated assembly 10 is shown to include an elongated carrier 11 such as a stick, and an applicator such as a swab 12. The applicator may comprise a sponge, or other porous material, at the forward end of the assembly. The applicator is used to locally apply fluid to a concealed body surface, such as the surface 13b of the cervix, during use of the assembly. FIG. 1 shows a user's finger and thumb 20 and 21 manipulating the assembly.

Controllable screening or treatment liquid supply means is provided at 14, between the forward end of the carrier 11 and the applicator 12. The test means 14 is adapted to be manually squeezed to effect controllable communication of contained liquid to the applicator or swab 12, for applying such liquid as to a local area or areas such as the cervix or vagina. Since the supply means or unit 14 is located between 11 and 12, it provides a test means incorporated in or on the assembly 10.

Figure 2:
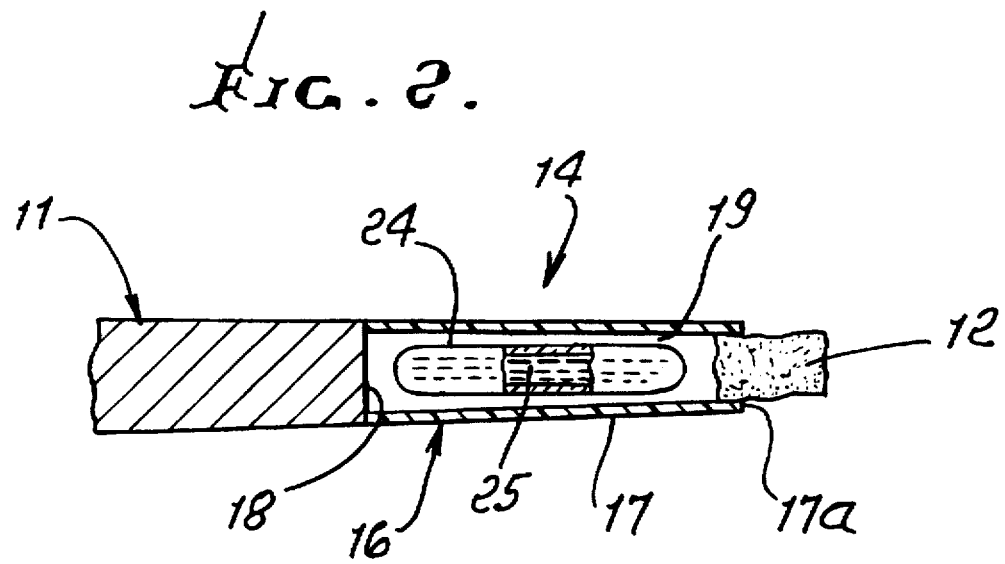
FIG. 2 is an enlarged section taken lengthwise through an end portion of the FIG. 1 assembly.

FIG. 2 shows the means or unit 14 as incorporating an outer container 16 which is elongated and tubular, having cylindrical side wall 17, and end wall 18 attached to the forward end of carrier 11 such as a stick. The interior 19 of the container communicates with applicator or swab 12, and for this purpose the swab may be received into the open forward end portion 17a of the outer container, thereby mounting the swab to the container.

A frangible inner container 24 is located within the interior 19 of container 16, and may be elongated, as shown.

Figure 3:
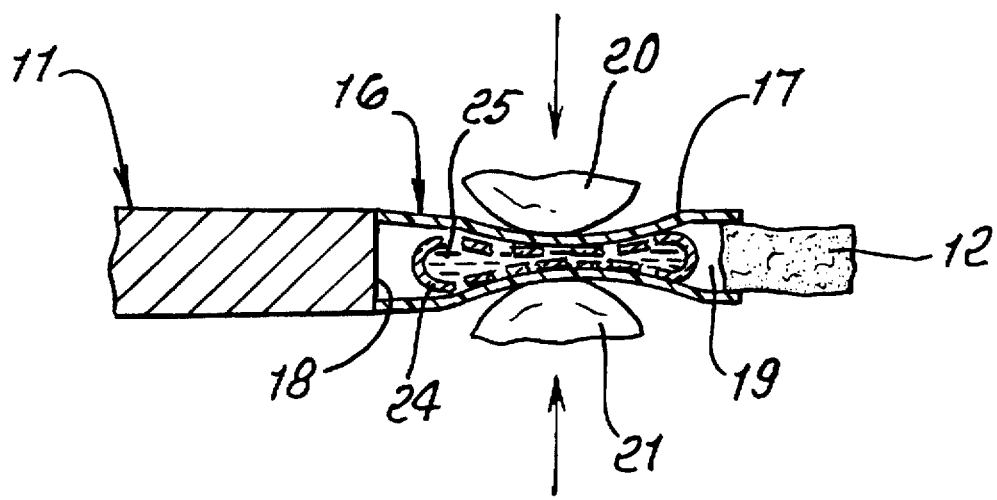
FIG. 3 is a view like FIG. 2, showing manual fracture or rupture of an inner container located within an outer container, as also seen in FIG. 2.
Figure 4:
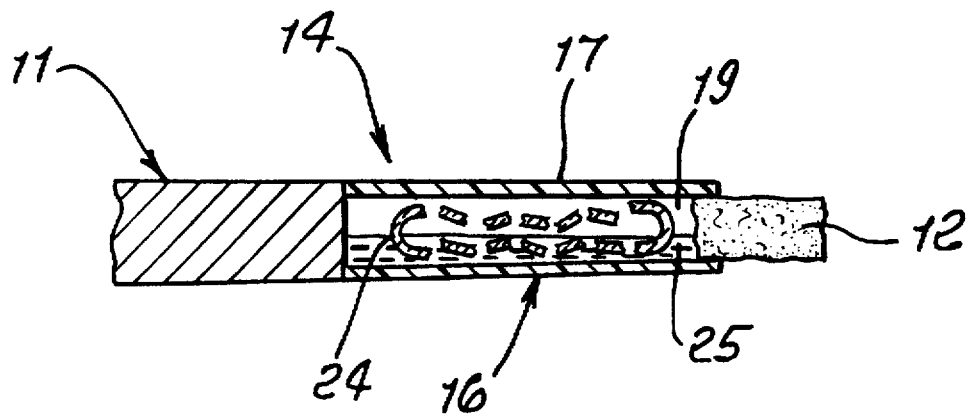
FIG. 4 is a view like FIG. 3, showing liquid from the inner container having been released into the interior of the outer container.
Figure 5:
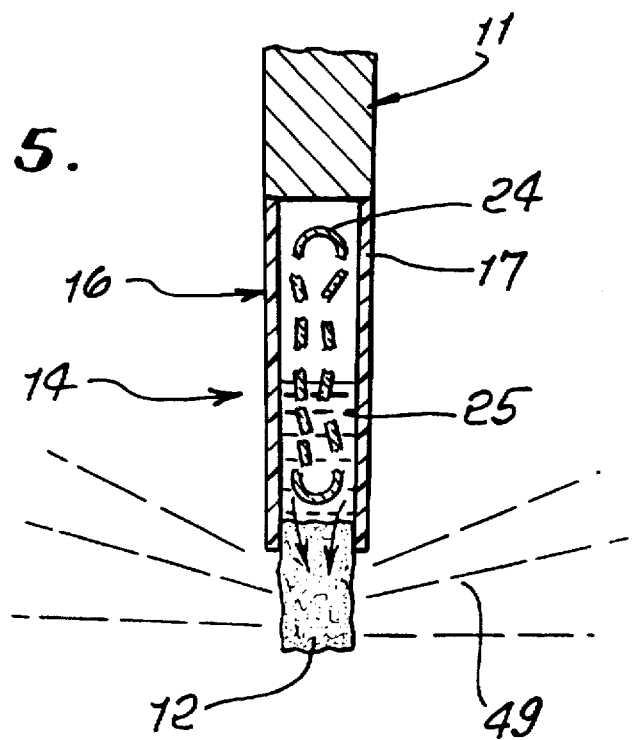
FIG. 5 is a view like FIG. 4, the fluid or liquid having flowed from the interior of the outer container to an applicator such as a swab at the end of the assembly, for use in applying such fluid or liquid to a concealed body part surface, such as the cervix.

Container 24 may consist of a hollow, thin-walled glass capsule to contain liquid 25. The outer container side wall 17 may consist of relatively stiff plastic material, which is sufficiently flexible to be squeezed, as by between user's finger and thumb 20 and 21, as seen in FIG. 3. Such squeezing, exerting pressure on the outer container, is sufficient to rupture the inner container as seen in FIG. 3, thereby releasing contained liquid 25 into the interior 19 of the outer container. See FIG. 4. This provides for controlled access of the treatment liquid to the swab, for application, as seen in FIG. 1. See also FIG. 5 orientation of the assembly 10 to cause gravitation of the liquid to flow into contact with the end of applicator or swab carried by the forward end portion of the outer container.

In one form of the invention, the screening liquid consists of dilute aqueous iodine solution, known as Lugol's or Shiller's solution, for reaction, as with the surface of the cervix. Such treatment causes a local discoloration of all normal tissue if no cancer cells are present, which may be observed by the physician. The user may thereby quickly and efficiently determine the existence of cervical pre-cancer or cancer, using a simple unitary screening test means and procedure as described, readily accessible to the cervix just after iodine release from storage. Another usable solution for this purpose consists of 10 parts Iodine, 30 parts Potassium Iodide and 350–500parts distilled water. Acetic acid solution may be employed, as referred to above.

Figure 6:
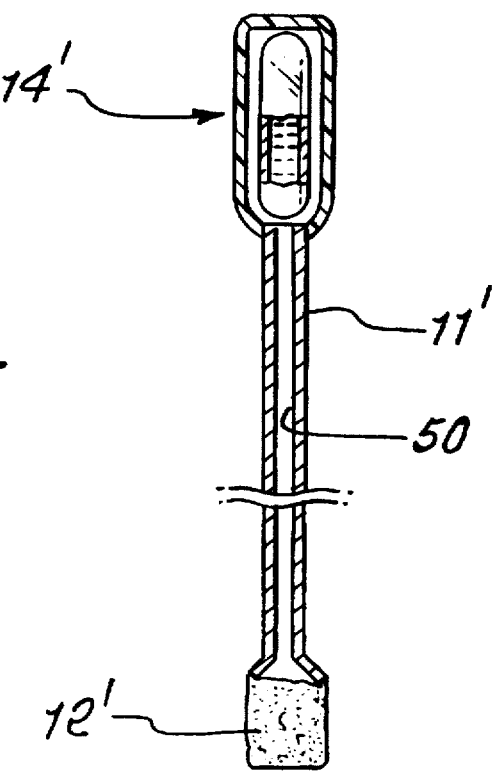
FIG. 6 is a view like FIG. 5, showing a modification.

FIG. 6 shows a modification in which the screening or treatment liquid supply means 14' is like 14, but located and supported at the opposite end of the carrier 11'. A duct 50 is provided in the carrier to communicate the released liquid to the swab 12'. The user can easily and conveniently manipulate the stick and swab, and also control test liquid delivery to the swab, from the remote or external end of the carrier. Note the reduced diameter of the carrier.

After such use, the carrier or stick is then disposable. Note that screening or treatment liquid is easily applied to a concealed body part or surface, without the user's fingers coming in contact with the screening liquid, such as iodine.

The apparatus may be used for treatment, as for example where treatment fluid such as podophyllum is released from the fractured inner container for application via the swab to treat human papilloma virus.

I claim:

1. In the method of applying screening or treatment fluid to tissue such as cervical tissue or vaginal tissue, the cervix, the steps that include:
   a) providing an elongated assembly including an elongated carrier and a flexible outer container supported on the carrier,
   b) providing a fluid applicator at one end of the assembly to communicate with the interior of the outer container,
   c) providing a frangible inner container protectively located within the outer container, and providing screening or treatment fluid within the inner container,
   d) exerting pressure on the outer container sufficient to rupture the inner container, thereby releasing said screening or treatment fluid into the interior of the outer container, enabling fluid migration to said applicator,
   e) and manipulating said assembly when inserted into the vaginal cavity to cause said applicator to apply said screening or treatment fluid to said tissue.

2. The method of claim 1 wherein said screening fluid consists essentially of one of the following:
   i) an aqueous iodine solution
   ii) an acetic acid solution.

3. The method of claim 2 including thereafter observing the tissue to determine tissue color change indicating pre cancer or cancer cells' presence in the unchanged area, and wherein normal tissue becomes a mahogany color while pre cancerous or cancerous tissue remains substantially unchanged.

4. The method of claim 1 wherein said outer container is provided in relatively close association with said applicator.

5. The method of claim 1 wherein said outer container is provided at a location on the carrier that is relatively remote from said applicator.

6. The method of claim 5 including providing an elongated duct carried by the carrier to convey fluid from the interior of the outer container to said applicator.

7. The method of claim 1 wherein said pressure is exerted manually.

8. The method of claim 7 including controlling said manual pressure to control the amount of screening or treatment fluid flow to the applicator.

9. The method of claim 7 including controlling said manual pressure to control fluid flow to the applicator.

10. The method of claim 1 including manipulating said assembly to cause the outer container to exert endwise and sidewise force on the applicator to cause the applicator to apply screening or treatment fluid to said tissue.

11. The method of claim 1 wherein said outer container is provided to consist of thin-walled flexible plastic material, and said inner container consists of glass.

12. The method of claim 1 wherein said applicator is provided to be carried by the outer container.

13. The method of claim 12 including inserting said applicator into an end of said outer container.

14. In apparatus for applying screening or treatment fluid to tissue such as cervical or vaginal tissue, the combination comprising:
   a) an elongated assembly including an elongated carrier and a flexible outer container supported on the carrier,
   b) a fluid applicator at one end of the assembly to communicate with the interior of the outer container,
   c) a frangible inner container protectively located within the outer container, and screening or treatment fluid contained within the inner container,
   d) whereby pressure exerted on the outer container sufficient to rupture the inner container effects release of said screening or treatment fluid into the interior of the outer container, enabling fluid migration to said applicator, whereby manipulation of said assembly when inserted into the vaginal cavity causes said applicator to apply said screening or treatment fluid to said tissue.

15. The combination of claim 14 wherein said screening or treatment fluid consists essentially of one of the following
   i) an aqueous iodine solution
   ii) an acetic acid solution
   iii) podophyllum.

16. The combination of claim 14 wherein said outer container is in relatively close association with said applicator.

17. The combination of claim 14 wherein said outer container is at a location on the carrier that is relatively remote from said applicator.

18. The method of claim 17 including an elongated duct carried by the carrier to convey fluid from the interior of the outer container to said applicator.

* * * * *